United States Patent [19]

Oyama et al.

[11] Patent Number: 4,534,909
[45] Date of Patent: Aug. 13, 1985

[54] PROCESS FOR PRODUCING A HALOGEN-CONTAINING ETHYLBENZENE DERIVATIVE

[75] Inventors: Kiyotaka Oyama, Hikari; Tuneo Harada, Shin-nanyo, both of Japan

[73] Assignee: Toyo Soda Manufacturing Co., Ltd., Shin-nanyo, Japan

[21] Appl. No.: 660,087

[22] Filed: Oct. 12, 1984

[30] Foreign Application Priority Data

Oct. 13, 1983 [JP] Japan .................. 58-189857

[51] Int. Cl.³ .................. C07C 121/66; C07C 69/76; C07C 53/134
[52] U.S. Cl. .................. 260/465 G; 560/105; 562/496; 564/182
[58] Field of Search .................. 260/465 G; 560/105; 562/496; 564/182

[56] References Cited

U.S. PATENT DOCUMENTS 4,145,362 3/1979 Brepoels et al. .................. 260/465 G

OTHER PUBLICATIONS

Brunner et al., Chemical Abstracts, vol. 44, 1054 (1950).
Kost et al., Chemical Abstracts, vol. 47, 2759 (1953).
Dombrovskii et al., Chemical Abstracts, vol. 51, 8038 (1957).
Dombrovskii et al., Chemical Abstracts, vol. 52, 9019 (1958).
Rondestvedt, Jr., Organic Reactions, vol. 24, pp. 225–259 (1976).

*Primary Examiner*—Dolph H. Torrence
*Attorney, Agent, or Firm*—Oblon, Fisher, Spivak, McClelland & Maier

[57] ABSTRACT

A process for producing a halogen-containing ethylbenzene derivative represented by the general formula:

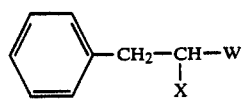

(I)

where X is a halogen atom, and W is a nitrile group, a carboxyl group, a lower alkoxycarbonyl group or an amidocarbonyl group, which comprises diazotizing aniline with a nitrite in a solution mixture comprising a hydrophilic organic solvent, an aqueous mineral acid solution and a vinyl compound represented by the general formula:

$$CH_2=CH-W \qquad (II)$$

where W is as defined above, to form a benzenediazonium salt, and reacting the benzenediazonium salt, without isolating it from the reaction system, with said vinyl compound in the presence of halogen ions and a copper compound as a catalyst.

19 Claims, No Drawings

PROCESS FOR PRODUCING A HALOGEN-CONTAINING ETHYLBENZENE DERIVATIVE

The present invention relates to a process for producing a halogen-containing ethylbenzene derivative. More particularly, the present invention relates to a process for producing a halogen-containing ethylbenzene derivative, which comprises diazotizing aniline, and reacting the diazonium salt with a vinyl compound and halogen ions in the presence of a catalyst.

Halogen-containing ethylbenzene derivatives such as α-halogeno-β-phenyl-substituted propionitriles, α-halogeno-β-phenyl-substituted propionic acids and their esters and amides, are useful substances, which can be converted to phenylalanine i.e. an important amino acid, by amination and, if necessary, hydrolysis. These halogen-containing ethylbenzene derivatives may be prepared by reacting a vinyl compound such as acrylonitrile, acrylic acid, an acrylate or an amide with a benzenediazonium salt and halogen ions.

Heretofore, in this method (i.e. a method using a so-called Meerwein reaction), it has been most common to conduct the reaction by using a copper compound catalyst in a solvent mixture comprising acetone and an aqueous hydrochloric acid solution and by adding sodium acetate (W. H. Brunner et at., Chemical Abstract, vol. 44, 1054h (1950); A. N. Kost et al., Chemical Abstract, vol. 47, 2759i (1953); A. V. Dombrovskii, Chemical Abstract, vol. 51, 8038f (1957), and ibid., vol. 52, 9019i (1958)). However, from the industrial point of view, this process has a problem in that it requires a great amount of sodium acetate.

On the other hand, R. Filler et al. have reported on a process for conducting the reaction in a solvent mixture comprising acetone and an aqueous hydrochloric acid solution without using sodium acetate. However, in this process, the yield is not high enough (Proc. Chem. Soc., 117 (1962) and Can. J. Chem., vol. 45, 329 (1967)).

On the other hand, the present inventors have found that the yield can be improved by using an excess amount of the vinyl compound relative to the benzenediazonium salt in the reaction in a solution mixture of a hydrophilic organic solvent and an aqueous mineral acid solution in the presence of halogen ions using a monovalent copper compound as a catalyst.

However, such a vinyl compound readily undergoes radical polymerization. For instance, acrylonitrile is known to undergo polymerization in the presence of a diazonium salt (S. C. Chiang et al., Chemical Abstract, vol. 67, 3691c (1966)). Therefore, in reacting such a vinyl compound with the benzenediazonium salt, particularly in its excess amount, it is an extremely important technical subject matter to prevent such a side reaction and to recover the excess amount of the vinyl compound without permitting any substantial polymerization. It is also important from the industrial point of view to establish a technique to economically recover and reuse the organic solvent used for the reaction.

Under these circumstances, the present inventors have conducted extensive researches for an industrial process for producing the desired halogen-containing ethylbenzene derivative from aniline and the vinyl compound, and as a result, have found the following facts.

(1) In the reaction of the diazonium salt with the vinyl compound (hereinafter referred to simply as "arylation reaction"), if the amount of water is excessive, the yield of the desired halogen-containing ethylbenzene derivative will be poor. On the other hand, if the amount of water is inadequate in the diazotization reaction, the mineral acid salt of aniline can not be dissolved, and the reaction mixture turns into a slurry, whereby it becomes difficult to remove heat for the exothermic diazotization reaction or to mix the reaction solution, and side reactions such as diazocoupling or a reaction for the formation of phenol, are likely to be led. Whereas, if the slurry is dissolved by an addition of a hydrophilic solvent and the reaction is conducted in a uniform system, the mixing and the heat removal will be facilitated, and side reactions will be controlled.

(2) As mentioned above, the vinyl compound such as acrylonitrile, readily undergoes radical polymerization. Namely, also in this reaction, the vinyl compound as the starting material was expected to be converted to a polymer. Surprisingly, however, in accordance with the process of the present invention, the major portion of the vinyl compound charged in excess remains unreacted in the reaction mixture.

(3) Even when the reaction of aniline with a nitrite such as sodium nitrite is conducted in the presence of the vinyl compound, the diazotization reaction is not substantially affected. Likewise, the vinyl compound itself is not susceptible to any change such as polymerization by the sodium nitrite or the diazonium salt formed by the diazotization reaction, and can be used for the arylation reaction in the second stage.

(4) The low boiling point vinyl compound such as acrylonitrile or acrylate can be recovered in good yield without polymerization, by distillation under normal pressure after the completion of the arylation reaction. At the same time, the low boiling point hydrophilic organic solvent can likewise be recovered by distillation. Thus, when the low boiling point hydrophilic organic solvent and the low boiling point vinyl compound are used, these two can be recovered simultaneously by distillation and may be returned to the first stage reaction for reuse without separating them.

The inventors have accomplished the present invention on the basis of the above discoveries.

Namely, according to the first aspect, the present invention provides a process for producing a halogen-containing ethylbenzene derivative represented by the general formula:

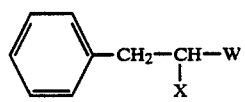
(I)

where X is a halogen atom, and W is a nitrile group, a carboxyl group, a lower alkoxycarbonyl group or an amidocarbonyl group, which comprises diazotizing aniline with a nitrite in a solution mixture comprising a hydrophilic organic solvent, an aqueous mineral acid solution and a vinyl compound represented by the general formula:

$$CH_2=CH-W \qquad (II)$$

where W is as defined above, to form a benzenediazonium salt, and reacting the benzenediazonium salt, without isolating it from the reaction system, with said vinyl compound in the presence of halogen ions and a copper compound as a catalyst.

The vinyl compound of the formula II which may be used in this process includes acrylonitrile, acrylic acid, and a lower alkyl ester and amide of acrylic acid. In the case where a lower alkyl ester of acrylic acid (i.e. in the case where an α-halogeno-βphenylpropionate is to be produced), the lower alkoxy moiety, i.e. the lower alkoxy moiety when Y in the general formulas I and II is a lower alkoxycarbonyl group, may be a methoxy group, an ethoxy group, a propoxy group or a butoxy group. A methoxy group or an ethoxy group is commonly employed.

As the aqueous mineral acid solution used for the diazotization in this process, there may be used an aqueous solution of a hydrohalogenic acid such as hydrochloric acid, hydrobromic acid or hydroiodic acid, or an oxygen acid such as sulfuric acid, nitric acid, phosphoric acid or perchloric acid, or an aqueous solution of a mixture thereof.

For the diazotization reaction in this process, an aqueous solution containing at least 2 mols of a mineral acid relative to 1 mol of aniline is used. However, in the second stage arylation reaction, if the amount of water is excessive, the yield of the arylation tends to decrease. Thus, the amount of the aqueous solution containing the mineral acid in the diazotization reaction solution is accordingly limited. Namely, the amount of the aqueous mineral acid solution is usually from 100 ml to 1.5 liters, preferably from 150 ml to 1 liter, more preferably from 200 ml to 600 ml, relative to 1 mol of aniline. If the hydrophilic organic solvent is not used, the anilinium salt formed by the reaction of aniline with the mineral acid, particularly in the region at the lower limit of the amount, tends to precipitate to form a slurry, whereby it will be extremely difficult to perform the mixing of the solution and to remove the heat of the reaction generated by the diazotization reaction, and side reactions such as the decomposition of the diazonium salt and diazocoupling are likely to take place. When the hydrophilic organic solvent is added at the time of the diazotization reaction to dissolve the slurry and a nitrite is added while maintaining the system to be uniform, no substantial side reactions take place and the reaction can be conducted satisfactorily.

Accordingly, as the organic solvent used for the first aspect of the present invention, it is preferred to employ an organic solvent which is hydrophilic and which is capable of dissolving the substantial portion of the mineral acid salt of aniline in the solution mixture with the aqueous mineral acid solution. Further, the organic solvent must be the one which does not hinder the diazotization reaction and the arylation reaction, and must be suitable for use in such reactions. As the solvent which satisfies these requirements, there may be mentioned a lower alcohol such as methanol, ethanol, propanol or butanol; an ether such as tetrahydrofuran, 1,4-dioxane or a mono- or di-alkyl ether of ethylene glycol; a ketone such as acetone, methyl ethyl ketone or methyl isobutyl ketone; and a non-proton organic polar solvent such as N,N-dimethylformamide, dimethyl sulfoxide or acetonitrile, or a solvent mixture thereof. The amount of the organic solvent is usually from 100 ml to 3 liters, preferably from 150 ml to 1.5 liters, more preferably from 200 ml to 1 liter, relative to 1 mol of aniline.

As the nitrite to be used, there may be mentioned sodium nitrite. It is common to use this nitrite in an amount of at least the stoichiometric amount relative to the aniline. If the amount is less than the stoichiometric amount, the diazotization yield tends to be poor. On the other hand, if the amount is excessive, it oxidizes the monovalent copper ions of the catalyst in the arylation reaction to the divalent ions, whereby a great amount of the copper catalyst will be required, such being uneconomical.

The nitrite is dissolved in water in an amount as small as possible, and while dropwise adding the solution thus obtained to the solution mixture of the hydrophilic organic solvent and the aqueous mineral acid solution containing aniline, the diazotization reaction is conducted under stirring. The temperature for the diazotization reaction is usually from about $-30°$ to about $30°$ C., preferably from about $-10°$ to about $20°$ C., more preferably from about $0°$ to about $10°$ C. The diazotization reaction is an exothermic reaction, and, in order to prevent side reactions, the reaction is conducted while cooling the reaction solution to maintain the temperature within the above-mentioned range. The reaction time is usually from about 30 minutes to about 24 hours including the time of the dropwise addition of the nitrite solution. It is common that reaction time is from 1 to 5 hours.

After the completion of the diazotization reaction, the copper compound as the catalyst is added, and the arylation reaction is conducted. When a ketone such as acetone is used as the hydrophilic organic solvent, a monovalent and divalent copper compounds may be used. However, when other hydrophilic organic solvents are used, it is preferred to employ a monovalent copper compound. As the copper compound, there may be used, for instance, cuprous oxide, cupric oxide, cuprous chloride, cupric chloride, cuprous bromide, cupric bromide, cuprous iodide, cupric iodide, cuprous cyanide, cupric cyanide, copper sulfate, copper nitrate or copper acetate. Among them, a monovalent copper compound such as cuprous oxide or cuprous chloride, is particularly preferred. The copper compound may be used in the form of powder, or it may be used as dissolved in a proper solvent. The amount of the catalyst is usually from about 0.005 to about 1 mol, preferably from about 0.01 to about 0.5 mol, more preferably from about 0.02 to about 0.2 mol, relative to 1 mol of the diazonium salt.

When a monovalent copper compound is used, the arylation reaction can be conducted without necessity of adjusting the pH so long as the reaction solution is under an acidic condition i.e. at a pH of 6 or less. Therefore, if halogen ions are present in the reaction system after the diazotization of aniline under an acidic condition with the mineral acid, the arylation reaction can be conducted successively after the diazotization reaction, simply by adding a monovalent copper compound to the reaction system. However, it is possible to conduct the arylation reaction under a weakly acidic condition after partially neutralizing the diazotized reaction solution with a weakly alkaline substance such as sodium acetate, sodium carbonate or sodium hydrogen carbonate. In the case where a divalent copper compound is used, it is preferred to add such a weakly alkaline substance and conduct the arylation reaction while maintaining the pH to a level of from 4 to 6.

For the formation of the halogen-containing ethylbenzene derivative according to the present invention, the halogen atoms are taken into the molecules of the product from the solution, and accoridngly, the halogen ions in the solution must be present in an amount of at least the stoichiometric amount relative to the diazonium salt. As the halogen ions, there may be mentioned chlorine ions, bromine ions and iodine ions. Accordingly, when the diazotization reaction is conducted by a mineral acid other than a hydrohalogenic acid, it is necessary to add a substance containing halogen ions to the reaction system before the arylation reaction. As such a substance, there may be employed hydrochloric acid, hydrobromic acid or hydroiodic acid, or a salt thereof with an inorganic or organic base.

In this process, the arylation reaction proceeds exothermically by the addition of the copper compound catalyst. The reaction is preferably conducted under cooling in order to avoid side reactions such as the decomposition of the diazonium salt or the polymerization of the vinyl compound. The reaction temperature is usually from about −30° to about 50° C., preferably from about −10° to about 40° C., preferably from about 0° to about 30° C. The catalyst should preferably be added portionwise or continuously at a rate to bring the reaction temperature to the above-mentioned range.

The amount of the vinyl compound used for the arylation reaction in this process, is theoretically an equimolar amount relative to the diazonium salt. However, in this process, the yield based on the diazonium salt is higher when the vinyl compound is used in excess. Accordingly, the vinyl compound is used usually in an amount of from about 1 to about 7 mols, preferably from about 1.5 to about 5 mols, relative to 1 mol of the diazonium salt.

According to the process of the first aspect of the present invention, after the completion of the arylation reaction, the desired halogen-containing ethylbenzene derivative can be recovered by a conventional method such as extraction.

According to the second aspect, the present invention provides a process for producing a halogen-containing ethylbenzene derivative, which comprises diazotizing aniline with a nitrite in a solution mixture comprising a hydrophilic organic solvent, an aqueous mineral acid solution and a low boiling point vinyl compound represented by the general formula:

$$CH_2=CH-Y \quad \text{(III)}$$

where Y is a nitrile group or a lower alkoxycarbonyl group, to form a benzenediazonium salt, then reacting the benzenediazonium salt, without isolating it from the reaction system, with said low boiling point vinyl compound and halogen ions in the presence of the halogen ions and a copper compound as a catalyst, to form a halogen-containing ethylbenzene derivative represented by the general formula:

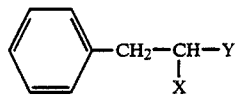
(IV)

where X is a halogen atom, and Y is as defined above, subjecting the reaction mixture to distillation to recover the unreacted low boiling point vinyl compound, and recovering the halogen-containing ethylbenzene derivative from the distillation residue.

The low boiling point vinyl compound of the formula III used in the process of the second aspect of the present invention, is specifically acrylonitrile or a lower alkyl ester of acrylic acid. A lower alkoxy moiety in the lower alkyl ester of acrylic acid, i.e. the lower alkoxy moiety in the case where Y in the general formulas III and IV is a lower alkoxycarbonyl group, may be a methoxy group, an ethoxy group, a propoxy group and a butoxy group. A methoxy group or an ethoxy group is commonly employed.

The aqueous mineral acid solution and its amount employed in the process of the second aspect of the present invention, are the same as employed in the process of the first aspect of the present invention.

The hydrophilic organic solvent and its amount employed in the process of the second aspect are the same as employed in the process of the first aspect. However, among them, a low boiling point hydrophilic organic solvent which can readily be recovered by distillation from the solution mixture after the completion of the arylation reaction, i.e. a hydrophilic organic solvent having a low boiling point by itself or a hydrophilic organic solvent which is capable of being azeotropically distilled with water or the vinyl compound of the formula III or with both solutions at a low azeotropic temperature, is particularly preferred. As the solvent which satisfies such conditions, there may be mentioned a lower alcohol such as methanol, ethanol, propanol or butanol; an ether such as tetrahydrofuran or 1,2-dimethoxyethane; a ketone such as acetone or methyl ethyl ketone; or a non-proton organic solvent such as acetonitrile.

When such a solvent is employed, it can be recovered simultaneously at the time of recovering the unreacted low boiling point vinyl compound by distillation.

The halogen ions are exactly the same as described with reference to the process of the first aspect of the present invention.

After the completion of the arylation reaction, the reaction solution normally forms two phase i.e. an organic phase containing the reaction product and an aqueous phase, According to the process of the second aspect of the present invention, such a reaction solution mixture is subjected to distillation as it is, or after separating the two phases, the respective phases are subjected to distillation separately, whereby the unreacted vinyl compound present in the reaction solution is recovered.

The recovered vinyl compound can be used as the starting material for either process of the present invention. When a low boiling hydrophilic organic solvent is used as the organic solvent, it can be recovered simultaneously with the vinyl compound, as mentioned above. The mixture of the vinyl compound and the organic solvent, thus recovered, may be reused as it is, as the starting material vinyl compound and organic solvent for either process of the present invention, or as a part of such starting materials.

From the residue after the removal of the organic solvent and the vinyl compound by distillation, the reaction product can be recovered by a conventional method such as extraction or distillation.

According to the processes of the present invention, a halogen-containing ethylbenzene derivative useful as an intermediate for phenylalanine can be produced from aniline and the vinyl compound in substantially higher yield than that attainable by the conventional techniques. Further, the respective starting materials can be efficiently recovered and reused.

Now, the present invention will be described in further detail with reference to Examples. However, it should be understood that the present invention is by no means restricted to these specific Examples.

EXAMPLE 1

While cooling and stirring a mixture comprising 55.8 g (0.6 mol) of aniline, 200 ml of a 25% hydrochloric acid aqueous solution, 200 ml of acetone and 95.4 g (1.8 mols) of acrylonitrile at a temperature of from 0° to 10° C., a solution prepared by dissolving 42.5 g (0.615 mol) of sodium nitrite in 85 ml of distilled water, was dropwise added thereto over a period of about 2 hours. After the completion of the dropwise addition, the mixture was further stirred for about 1 hour at the same temperature. Then, while cooling the reaction mixture from outside to maintain it at the same temperature, 5 g of cuprous oxide powder was gradually added under stirring. After the completion of the addition, the mixture was stirred at a temperature of from 10° to 20° C. for further about 2 hours. Then, the reaction solution was analyzed by gas chromatography, whereby it was found that α-chloro-β-phenylpropionitrile formed in a yield of 89%.

EXAMPLES 2 TO 8

The reactions were conducted in the same manner as in Example 1 except that various solvents were used instead of acetone. The results are shown in Table 1.

TABLE 1

| Example No. | Solvent and its amount (ml) | Yield (%) |
|---|---|---|
| 2 | Methanol 400 | 88 |
| 3 | Ethanol 200 | 86 |
| 4 | Isopropanol 200 | 83 |
| 5 | Acetonitrile 200 | 86 |
| 6 | Tetrahydrofuran 200 | 85 |
| 7 | N,N—dimethylformamide 200 | 87 |
| 8 | Dimethylsulfoxide 200 | 77 |

EXAMPLE 9

The reaction was conducted in the same manner as in Example 1 except that the cuprous oxide powder in Example 1 was changed to 25 ml of a conc. hydrochloric acid aqueous solution containing 5 g of cuprous chloride. The yield of α-chloro-β-phenylpropionitrile was 89%.

EXAMPLE 10

The reaction was conducted in the same manner as in Example 1 except that in Example 1, 300 ml of 40% sulfuric acid was used instead of 200 ml of the 25% hydrochloric acid aqueous solution, and 40 g of sodium chloride was added after the completion of the diazotization reaction. The yield of α-chloro-β-phenylpropionitrile was 83%.

EXAMPLE 11

The reaction was conducted in the same manner as in Example 1 except that in Example 1, methyl acrylate, acrylamide or acrylic acid was used instead of acrylonitrile, and methanol was used instead of acetone. The results are shown in Table 2.

TABLE 2

| Example No. | Vinyl compound and its amount (g) | Yield (%) |
|---|---|---|
| 12 | Methyl acrylate 155 | 60 |
| 13 | Acrylic acid amide 128 | 57 |
| 14 | Acrylic acid 130 | 52 |

EXAMPLE 15

The reaction was conducted in the same manner as in Example 1 except that in Example 1, 300 ml of a 30% hydrobromic acid aqueous solution was used instead of the 25% hydrochloric acid aqueous solution, and 400 ml of methanol was used instead of acetone. After the completion of the reaction, the reaction solution was analyzed by gas chromatography, whereby it was found that α-bromo-β-phenylpropionitrile formed in a yield of 70%.

EXAMPLE 16

In Example 1, after the completion of the reaction with the cuprous oxide, the reaction mixture was distilled under normal pressure, whereby a liquid containing 62 g of acrylonitrile and 185 ml of acetone (the recovery rates based on the respective feeds, were 65% and 95%, respectively, was recovered as the distillate. The recovered acrylonitrile and acetone were subjected to the same operation as above after supplementing the deficit amounts. The yield of α-chloro-β-phenylpropionitrile in the second reaction was 86%.

EXAMPLES 17 TO 21

In each of Examples 2, 3, 4, 5 and 6, acrylonitrile and the solvent were recovered, and the reactions were repeated by using them in the same manner as in Example 16. The results thereby obtained are shown in Table 3.

TABLE 3

| Example No. | Recovery rate (%) Acrylonitrile | Recovery rate (%) Solvent | Yield by the repeated reaction |
|---|---|---|---|
| 17 | 67 | 95 | 88 |
| 18 | 62 | 90 | 88 |
| 19 | 55 | 85 | 85 |
| 20 | 56 | 83 | 82 |
| 21 | 56 | 85 | 83 |

EXAMPLE 22

In Example 12, methyl acrylate and methanol were recovered, and the reaction was repeated by using them in the same manner as in Example 16.

The recovery rates of methyl acrylate and methanol were 57% and 95%, respectively. The yield of methyl α-chloro-β-phenylpropionate by the repeated reaction was 57%.

We claim:

1. A process for producing a halogen-containing ethylbenzene derivative represented by the general formula:

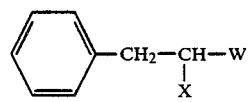  (I)

where X is a halogen atom, and W is a nitrile group, a carboxyl group, a lower alkoxycarbonyl group or an amidocarbonyl group, which comprises diazotizing aniline with a nitrite in a solution mixture comprising a hydrophilic organic solvent, an aqueous mineral acid solution and a vinyl compound represented by the general formula:

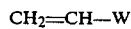  (II)

where W is as defined above, to form a benzenediazonium salt, and reacting the benzenediazonium salt, without isolating it from the reaction system, with said vinyl compound in the presence of halogen ions and a copper compound as a catalyst.

2. The process according to claim 1, wherein the hydrophilic organic solvent is a lower alcohol, a hydrophilic ether, a hydrophilic ketone or other non-proton hydrophilic organic polar solvent.

3. The process according to claim 2, wherein the hydrophilic organic solvent is methanol, ethanol, propanol or butanol.

4. The process according to claim 2, wherein the hydrophilic organic solvent is tetrahydrofuran, 1,4-dioxane or a mono- or di-alkyl ether of ethylene glycol.

5. The process according to claim 2, wherein the hydrophilic organic solvent is acetone or methyl ethyl ketone.

6. The process according to claim 2, wherein the hydrophilic organic solvent is N,N-dimethylformamide, dimethyl sulfoxide or acetonitrile.

7. The process according to claim 1, wherein the aqueous mineral acid solution is an aqueous hydrohalogenic acid solution, an aqueous oxygen acid solution or a mixture thereof.

8. The process according to claim 1, wherein the halogen ions are chlorine, bromine or iodine ions.

9. The process according to claim 1, wherein the copper compound as the catalyst is a monovalent copper compound.

10. A process for producing a halogen-containing ethylbenzene derivative, which comprises diazotizing aniline with a nitrite in a solution mixture comprising a hydrophilic organic solvent, an aqueous mineral acid solution and a low boiling point vinyl compound represented by the general formula:

$$CH_2=CH-Y \qquad (III)$$

where Y is a nitrile group or a lower alkoxy carbonyl group, to form a benzenediazonium salt, then reacting the benzenediazonium salt, without isolating it from the reaction system, with said low boiling point vinyl compound and halogen ions in the presence of the halogen ions and a copper compound as a catalyst, to form a halogen-containing ethylbenzene derivative represented by the general formula:

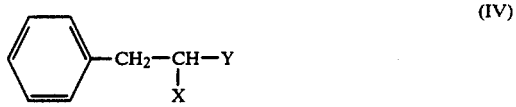

where X is a halogen atom, and Y is as defined above, subjecting the reaction mixture to distillation to recover the unreacted low boiling point vinyl compound, and recovering the halogen-containing ethylbenzene derivative from the distillation residue.

11. The process according to claim 10, wherein a low boiling point hydrophilic organic solvent is used as the hydrophilic organic solvent, and after the completion of the reaction, the reaction mixture is distilled to recover the organic solvent together with the vinyl compound.

12. The process according to claim 11, wherein the low boiling point hydrophilic organic solvent is a low boiling point lower alcohol, a hydrophilic ether, a hydrophilic ketone or other non-proton hydrophilic organic polar solvent.

13. The process according to claim 12, wherein the low boiling point hydrophilic organic solvent is methanol, ethanol, propanol or butanol.

14. The process according to claim 12, wherein the low boiling point hydrophilic organic solvent is tetrahydrofuran or 1,2-dimethoxyethane.

15. The process according to claim 12, wherein the low boiling point hydrophilic organic solvent is acetone or methyl ethyl ketone.

16. The process according to claim 12, wherein the low boiling point hydrophilic organic solvent is acetonitrile.

17. The process according to claim 10, wherein the aqueous mineral acid solution is an aqueous hydrohalogenic acid solution, an aqueous oxygen acid solution or a mixture thereof.

18. The process according to claim 10, wherein the halogen ions are chlorine, bromine or iodine ions.

19. The process according to claim 10, wherein the copper compound as the catalyst is a monovalent copper compound.

* * * * *